United States Patent
Schmiedel et al.

(10) Patent No.: US 7,531,498 B2
(45) Date of Patent: May 12, 2009

(54) PEROXYCARBOXYLIC ACID-BASED BLEACH COMPOSITIONS HAVING A LONG SHELF LIFE

(75) Inventors: Peter Schmiedel, Duesseldorf (DE); Paula Barreleiro, Hilden (DE); Wolfgang von Rybinski, Duesseldorf (DE); Bernhard Orlich, Barcelona (ES)

(73) Assignee: Henkel Kommanditgesellschaft auf Aktien (Henkel KGaA), Dusseldorf (DE)

( * ) Notice: Subject to any disclaimer, the term of this patent is extended or adjusted under 35 U.S.C. 154(b) by 288 days.

(21) Appl. No.: 11/299,795

(22) Filed: Dec. 12, 2005

(65) Prior Publication Data

US 2006/0178285 A1 Aug. 10, 2006

Related U.S. Application Data

(63) Continuation of application No. PCT/EP2004/006167, filed on Jun. 8, 2004.

(30) Foreign Application Priority Data

Jun. 13, 2003 (DE) .................. 103 27 127
Dec. 22, 2003 (DE) .................. 103 61 084

(51) Int. Cl.
C11D 7/38 (2006.01)
C11D 7/54 (2006.01)
C11D 17/00 (2006.01)

(52) U.S. Cl. .................. 510/441; 510/349; 510/375; 424/452; 264/4.1

(58) Field of Classification Search .................. 510/349, 510/375, 441; 424/452; 264/4.1
See application file for complete search history.

(56) References Cited

U.S. PATENT DOCUMENTS

| | | | |
|---|---|---|---|
| 3,494,786 A | 2/1970 | Nielsen |
| 3,494,787 A | 2/1970 | Lund et al. |
| 4,094,808 A | 6/1978 | Stewart et al. |
| 4,126,573 A | 11/1978 | Johnston |
| 5,049,298 A | 9/1991 | Pioumen et al. |
| 5,230,822 A | 7/1993 | Kamel |
| 5,597,791 A | 1/1997 | Richards |
| 5,707,953 A | 1/1998 | Van't Land et al. |
| 6,080,710 A | 6/2000 | Withenshaw et al. |
| 6,080,715 A | 6/2000 | Bianchi |
| 6,534,091 B1 | 3/2003 | Garces Garces |
| 6,699,501 B1 | 3/2004 | Neu |
| 2003/0180369 A1 | 9/2003 | Grisoni |
| 2004/0013738 A1 | 1/2004 | Voigt |
| 2004/0247664 A1 | 12/2004 | Dreja |
| 2006/0172909 A1 | 8/2006 | Schmiedel |

FOREIGN PATENT DOCUMENTS

| | | |
|---|---|---|
| CA | 2 326 560 | 5/2001 |
| CH | 363329 | 7/1962 |
| DE | 199 54 959 | 5/2001 |
| DE | 10100689 | 7/2002 |
| DE | 101 57 755 | 6/2003 |
| EP | 0 272 402 | 6/1988 |
| EP | 0 294 206 | 12/1988 |
| EP | 0 334 404 | 9/1989 |
| EP | 0 334 405 | 9/1989 |
| EP | 0 337 516 | 10/1989 |
| EP | 0 435 379 | 7/1991 |
| EP | 0 442 549 | 8/1991 |
| EP | 0 510 761 | 10/1992 |
| EP | 0 653 485 | 5/1995 |
| EP | 0 691 398 | 1/1996 |
| GB | 1 156 240 | 6/1969 |
| GB | 2 032 421 | 5/1980 |
| WO | WO 94/13776 | 6/1994 |
| WO | WO 94/15010 | 7/1994 |
| WO | WO 97/39097 | 10/1997 |
| WO | WO 99/47252 | 9/1999 |
| WO | WO 01/01927 | 1/2001 |
| WO | WO 01/51196 | 7/2001 |
| WO | WO 02/17888 | 3/2002 |
| WO | WO 02/24319 | 3/2002 |
| WO | WO 02/31092 | 4/2002 |
| WO | WO 03/002248 | 1/2003 |
| WO | WO03/045545 * | 6/2003 |
| WO | WO 03/045545 | 6/2003 |

OTHER PUBLICATIONS

U.S. Appl. No. 11/299,166, filed Dec. 9, 2005, Schmiedel.
Terech, et al., "Low molecular mass gelators of organic liquids and the properties of their gels," Chem. Rev., No. 97:3133-3159 (1997).
Abdallah, et al., "Organogels and low molecular mass organic gelators," Adv. Mater., No. 12:1237-1247 (2000).

* cited by examiner

*Primary Examiner*—Gregory R Del Cotto
(74) *Attorney, Agent, or Firm*—John S. Child, Jr.

(57) ABSTRACT

A gel capsule, loaded with at least one organic percarboxylic acid is manufactured by the process comprising the steps of: (a) providing an oil having a melting point below 35° C. at atmospheric pressure and that is inert towards the organic percarboxylic acid; (b) contacting the oil with at least one stabilizer at a temperature of from 25° C. to 50° C. to obtain a liquid matrix medium comprising the oil and the stabilizer, (c) optionally cooling the matrix medium resulting from step (b) to a temperature above the gel-formation temperature of the matrix medium; (d) incorporating at least one organic percarboxylic acid in the form of solid particles into the liquid matrix medium obtained in step (b) to form a dispersion of the solid percarboxylic acid in the liquid matrix medium; (e) contacting the matrix medium obtained in process step (d), with a dispersion agent at a temperature below the gel-formation temperature to form gel capsules, wherein the organic percarboxylic acid is incorporated in an oil/stabilizer-gel matrix.

23 Claims, No Drawings

PEROXYCARBOXYLIC ACID-BASED BLEACH COMPOSITIONS HAVING A LONG SHELF LIFE

CROSS-REFERENCE TO RELATED APPLICATIONS

This application is a continuation under 35 U.S.C. § 365(c) and 35 U.S.C. § 120 of international application PCT/EP2004/006167, filed Jun. 8, 2004, which is incorporated herein by reference in its entirety. This application also claims priority under 35 U.S.C. § 119 of DE 103 27 127.9, filed Jun. 13, 2003, and of DE 103 61 084.7, filed Dec. 22, 2003, each of which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a process for the manufacture of a gel capsule loaded with at least one organic percarboxylic acid, as well as the gel capsules manufactured in this manner. Furthermore, the present invention relates to the use of these gel capsules as bleaching agents or components of bleaching agents, particularly for their use in washing and cleaning agents, particularly in liquid washing and cleaning agents, tooth-care products, hair colorants and decolorizing or bleaching agent compositions for technical uses, as well as the products comprising these gel capsules, i.e. washing and cleaning agents, particularly liquid washing and cleaning agents, tooth-care products, hair colorants and decolorizing or bleaching agent compositions for technical uses, which comprise the inventive gel capsules.

For liquid, particularly aqueous washing and cleaning agents that are enjoying an increased popularity due to their positive product properties, such as a better and faster solubility and practicality, the addition to the formulation or incorporation of bleaching (agent) components is problematic for numerous reasons. Due to their decomposition reactions or hydrolysis and incompatibilities towards other constituents of the washing agent formulation, such as, e.g., enzymes or surfactants, the added bleaching agents often lose their activity already on storage or even during product utilization. An adverse consequence resulting from this, is that the washing performance—particularly the bleaching power—of the washing agent formulation noticeably deteriorates, such that bleachable stains in particular can no longer be satisfactorily removed.

Bleaching agents, such as for example perborates or percarbonates, which are usually used in solid washing agent formulations, are extremely moisture sensitive, with the result that they often lose their bleaching power within a few days in a liquid and particularly aqueous washing or cleaning agents, due to the loss of active oxygen.

On the other hand, percarboxylic acids, especially imidopercarboxylic acids, the most important representative of which is phthalimidopercapric acid (PAP), are more efficient and less sensitive to hydrolysis and are known in the prior art as bleaching agents for washing and cleaning agents. Nevertheless, their storage stability is by far insufficient to guarantee a long-term use of the corresponding washing and cleaning agent without the consequent loss in activity. The addition of percarboxylic acids, particularly imidopercarboxylic acids, in liquid washing and cleaning agents is therefore particularly problematic.

Because of the disadvantages that result from a modification of the washing and cleaning agent formulation as a consequence of the decomposition of imidopercarboxylic acids, particularly PAP, attempts have been made in the prior art to efficiently encapsulate the imidopercarboxylic acids (e.g., PAP), such that the imidopercarboxylic acid cannot come into contact with the rest of the components of the washing or cleaning agents.

(2) Description of Related Art, Including Information Disclosed Under 37 C.F.R. §§ 1.97 and 1.98

Thus, EP 0 510 761 B1 or U.S. Pat. No. 5,230,822, which belongs to the same patent family, describes a process for encapsulating washing agent additives in general, such as enzymes, bleaching agents, comprising inter alia PAP, bleaching agent precursors and bleach catalysts, wherein a wax with a melting point between 40° C. and 50° C. is used as the protective shell for the encapsulation. The coated washing particle is manufactured by spraying molten wax onto the particles. For this, the wax must first be heated to temperatures above its melting point; this can sometimes be deleterious for the substances being encapsulated. This process has also the disadvantage that the active substance will be released only at temperatures above the melting point of the applied wax—therefore only above temperatures between 40° C. and 50° C. This particularly falls short of the requirements of today's consumer or user, as—bearing in mind the development of higher performance washing and cleaning agent formulations and the saving in energy costs—washing should also be often carried out at lower temperatures, particularly at about 30° C. Moreover, a wax with a high melting point has the disadvantage that, particularly at low temperatures, it leaves residues on the washing, as it is not completely emulsified at these temperatures.

EP 0 653 485 A1 relates to capsule compositions of active substances that can comprise, inter alia, bleaching agents, such as PAP, and in which the active substance inside the capsule is present as a dispersion in oil. The manufacture of these capsules, whose shell is formed of polymers that only dissolve during the washing process or the application, necessitates an expensive and technologically non-trivial operation of an emulsification process.

WO 03/045545 A1 describes capsules that contain active substances and which are produced by means of a mini emulsion process using a carrier phase and a block copolymer. The mentioned active substances have to be dissolved in the oil phase, with the result that the described capsule systems are largely restricted to active substances soluble in the oil phase, particularly hydrophobic active substances. Bleaching agents are not mentioned here. A high-pressure homogenization is required to manufacture the mini emulsion.

BRIEF SUMMARY OF THE INVENTION

Against this background, the object of the present invention therefore consists in providing percarboxylic acids, particularly imidopercarboxylic acids, such as phthalimidopercapric acid (PAP) in storage stable form.

A further object consists in providing an inclusion or encapsulation or coating of percarboxylic acids, particularly imidopercarboxylic acids, such as phthalimidopercapric acid (PAP) with improved properties in comparison with the prior art, as well as an appropriate manufacturing process.

Another further object of the present invention is the provision of gel capsules that are loaded with solid percarboxylic acids and which lead to a good stabilization of the percarboxylic acid and hence to an improved storage stability. In particular, it is intended in the scope of the present invention to provide an encapsulation that particularly during the washing process even at low temperatures will be dissolved or solubilized largely without residues, such that the release of the percarboxylic acid will not be hindered and at the same time, residues on the washing will be avoided. In particular, such a process is intended to enable production of gel capsules loaded with at least one percarboxylic acid as the active substance and which at least largely avoid the previously highlighted disadvantages of the prior art. Thus, with respect to the manufacture of the gel capsules, it is intended to ensure that the fewest possible starting material(s) for building the gel capsule are used, such that a high content of active substance is realizable.

Yet another object of the invention is a process for the manufacture of a gel capsule, loaded with at least one organic percarboxylic acid comprising the steps of: (a) providing an oil having a melting point below 35° C. at atmospheric pressure and that is inert towards the organic percarboxylic acid; (b) contacting the oil with at least one stabilizer at a temperature of from 25° C. to 50° C. to obtain a liquid matrix medium comprising the oil and the stabilizer, (c) optionally cooling the matrix medium resulting from step (b) to a temperature above the gel-formation temperature of the matrix medium; (d) incorporating at least one organic percarboxylic acid in the form of solid particles into the liquid matrix medium obtained in step (b) to form a dispersion of the solid percarboxylic acid in the liquid matrix medium; (e) contacting the matrix medium obtained in process step (d), with a dispersion agent at a temperature below the gel-formation temperature to form gel capsules, wherein the organic percarboxylic acid is incorporated in an oil/stabilizer-gel matrix.

BRIEF DESCRIPTION OF THE SEVERAL VIEWS OF THE DRAWING(S)

Not Applicable

DETAILED DESCRIPTION OF THE INVENTION

Applicants have now surprisingly found that organic percarboxylic acids, such as imidopercarboxylic acids (e.g., PAP) can be stabilized using a gel capsule matrix based on hardened or gelled oil phases.

According to a first aspect, the subject of the present invention is therefore a process for the manufacture of gel capsules, loaded with at least one organic percarboxylic acid, particularly imidopercarboxylic acid, in which at least one organic percarboxylic acid, particularly imidopercarboxylic acid, is incorporated in the form of solid particles into a gel matrix based on an oil phase that is inert towards the organic percarboxylic acid and hardened and/or gelled by means of the addition of at least one stabilizer, particularly gel-formers, wherein the melting point of the oil phase is below 35° C. at atmospheric pressure, particularly by means of an encapsulation and/or coating surrounding the percarboxylic acid.

According to the invention, in this way there result gel capsules, whose capsule shells are based on a gel matrix and capsule core that comprise at least one organic percarboxylic acid. Each of the inventive gel capsules can also possess a plurality of capsule cores; in particular agglomerates of percarboxylic acid particles can be formed during the production. An agglomeration of a plurality of gel capsules is also possible. In this manner, so to speak, a matrix results, in which a plurality of capsule cores are embedded or incorporated.

In particular, the present invention relates to a process for the manufacture of a gel capsule, loaded with at least one organic percarboxylic acid, particularly imidopercarboxylic acid, and which comprises the following process steps:

(a) Providing an oil phase that is inert towards the organic percarboxylic acid and hardened and/or gelled by means of the addition of a stabilizer, particularly gel-formers, wherein the melting point of said oil phase is below 35° C. at atmospheric pressure (101325 Pa); then (b) Contacting the oil phase with at least one stabilizer, particularly gel formers, preferably at a temperature above the gel-formation temperature, such that a preferably liquid matrix medium, based on the oil phase and stabilizer, particularly a gel-former, provided by process step (a) is obtained.

(c) Optionally cooling the matrix medium resulting from process step (b), preferably to temperatures above the gel-formation temperature of the matrix medium; then (d) Incorporating at least one organic percarboxylic acid to be stabilized and in the form of solid particles into the liquid matrix medium obtained in process step (b), preferably tempered in process step (c) to temperatures preferably above the gel-forming temperature, such that there results a dispersion of the solid percarboxylic acid in the preferably liquid matrix medium; then (e) Incorporation of the matrix medium obtained in process step (d), containing the incorporated, dispersed, solid particles of the organic percarboxylic acid for stabilization, into a dispersion agent, particularly water, preferably at temperatures below the gel-formation temperature and/or preferably with milling, particularly by the provision of shear forces, such that gel capsules, are obtained preferably in aqueous dispersion, based on at least one organic percarboxylic acid incorporated in an oil phase/stabilizer-gel matrix or encapsulated or coated herewith, wherein optionally the size of the gel capsule can be controlled by the milling, particularly by the provision of shear forces; then (f) optionally removing, the dispersion agent, particularly water, and any excess oil phase from the gel capsule dispersion obtained from process step (e) particularly by centrifugation and/or filtration, finally (g) optionally drying the gel capsules obtained in this way.

In the inventive process, organic percarboxylic acids are particularly employed as the substances to be stabilized, particularly to be encapsulated or to be coated. The percarboxylic acids may be selected from organic mono or dipercarboxylic acids. Examples are particularly dodecaneperdioic acid or preferably imidopercarboxylic acids, particularly preferably 6-phthalimidopercapric acid (6-phthalimidoperhexanoic acid, PAP). Advantageously the percarboxylic acid should have a melting point above 25° C., particularly above 35° C., in preference above 45° C., preferably above 50° C., particularly preferably above 100° C.; in this way it is assured that the percarboxylic acid used is mainly present as solid particles, such that in the scope of the inventive process a degradation of the percarboxylic acid in the course of the production of the gel capsules is at least largely avoided or reduced.

In general, the additional components, which are used in the inventive process for manufacturing the gel capsules, should be chosen with the proviso that they are at least largely compatible with respect to the percarboxylic acids being encapsulated or coated, i.e. there should be no unwanted chemical reactions, such as in particular degradation, oxidation or reduction and/or hydrolytic reactions between these components and the percarboxylic acid and none induced by the additional components on the percarboxylic acid that would lead in particular to its decomposition.

In the scope of the inventive process, the gelable or hardenable oil phase provided in process step (a) may particularly be selected from the group pf paraffin oils, isoparaffin oils, silicone oils, glycerides, triglycerides, naphthalene-containing oils, hydrocarbon-containing solvents and their mixtures, vegetal oils, castor oil, maize oil, peanut oil, alkyl palmitates and alkyl alcohol benzoates. According to the invention, paraffin oils are particularly preferred. Moreover, the melting point of the gellable or hardenable oil phase (i.e. the pure, i.e. non-gelled or non-hardened oil phase) should be $\leq 30°$ C., particularly $\leq 25°$ C. and preferably $\leq 20°$ C. at atmospheric pressure, such that in the scope of the inventive process, the gellable or hardenable oil phase is present in liquid form. In other words, this means that the inventively added pure oil phase is present in liquid form at temperatures above 35° C., particularly above 30° C., advantageously above 25° C., preferably above 20° C., such that it can be solubilized or dispersed without problem in a washing process by the other washing or cleaning agent constituents. In this context, a gellable or hardenable oil phase is understood to mean such an oil phase, which can form a gel or a gel matrix with a stabilizer, particularly gel formers, or can lead to a hardened (e.g., to a chemically and/or physically crosslinked) structure with a stabilizer. According to the invention, paraffins with a broad melting range and fractions that are also present as liquids below 30° C. are particularly preferred, as they are more easily dispersed in a washing process.

The stabilizer used in the inventive process, particularly gel formers, can be a block copolymer. The block copolymer can be in particular a hydrophobic, an organic block polymer formed with the gellable or hardenable oil phase below the corresponding gel-formation temperature, a gel or an oil phase/stabilizer-gel matrix, particularly organogels. Metal soaps, alkyl hydroxybutyramides and layered silicates are suitable as stabilizers, particularly gel formers. According to the invention, the compounds listed in the articles by Terech et al., Chem. Rev., Nr. 97, pages 3133 to 3159 (1997) and Abdallah et al., Adv. Mater., Nr. 12, N 17, pages 1237 to 1247 (2000) can also be added as stabilizers or gel formers, the total contents of the disclosed articles being incorporated here for reference. The stabilizer or gel former can be selected, for example, from fatty acid derivatives, fatty alcohols, steroid derivatives, anthryl derivatives, α-amino acid derivatives, organometallic compounds and dibenzylidene-D-sorbitol (DBS).

In the context of the present invention, gels are particularly understood to mean organogels in the form of dimensionally stable, easily deformable, disperse systems rich in liquids, which consist of at least two components, namely, in particular the gelable or hardenable oil phase that acts as the dispersion agent, and the stabilizer, in particular block copolymers as gel formers or gelling agents.

Without wishing to be bound by any particular theory, the formation of the gel matrix in process step (e) proceeds due to the physical interactions between the oil phase and the stabilizer, particularly gel formers. In particular, the stabilizer, particularly the gel former, forms a three-dimensional network in the dispersion agent i.e. in the oil phase, wherein the particles stick to one another in various places, such that a composite is formed as a result of largely physical interactions. The inventively manufactured gels or gel capsules possess a flow limit and in particular are elastically and/or plastically deformable. Below a gel formation temperature $T_{gel}$, also known as the gelation temperature and characteristic for each gel, this composite of gel-former and dispersion agent (=oil phase) forms a gel-type structure, which becomes liquid at temperatures above this gel-formation temperature.

The block copolymer, added according to the invention as the stabilizer or gel former, is especially a copolymer having gelling properties towards the gellable or hardenable oil phase used in the inventive process.

The inventively used block copolymer can be a polymer (A-B- . . . )$_n$ consisting of at least two blocks or components A and B, (n=the number of repeat units), in which at least one of the blocks is a harder block and at least another of the blocks is a softer block, which differ in their hardness as a result of their ratio, the hardness being measured particularly by means of their glass transition temperatures.

The inventively used block copolymer can be a polymer consisting of at least two blocks or components. At least one of the blocks can be a harder block and at least another of the blocks can be a softer block. The glass transition temperatures of the hard and soft blocks should differ by at least 50° C., particularly by at least 60° C., preferably by at least 70° C. The hard block, for example, can exhibit a glass transition temperature $T_{g(hard)}>20°$ C., particularly $T_{g(hard)}>50°$ C., preferably $T_{g(hard)}>90°$ C., whereas the soft block can exhibit a glass transition temperature $T_{g(soft)}\leq 20°$ C., particularly $T_{g(soft)}\leq 0°$ C., preferably $T_{g(soft)}\leq -45°$ C.

At least one block of the block copolymer, preferably the hard block should be not, or only poorly oil-soluble or at best slightly oil-soluble, whereas at least one other block of the block copolymer, preferably the soft block, should be designed as oil-soluble. In particular, at least one block of the block copolymer, preferably the hard block, should be less oil-soluble than at least one other block of the block copolymer, preferably the soft block.

The hard block of the block copolymer can preferably be selected from the group of polystyrene, poly(meth)acrylates, polycarbonates, polyesters, polyanilines, poly-p-phenylenes, polysulfone ethers, polyacrylonitriles, polyamides, polyimides, polyethers, polyvinyl chlorides and mixtures thereof. The soft block of the block copolymer can be selected from the group of rubbers, particularly optionally substituted polyalkylenes, preferably polybutadienes, and mixtures of rubbers or polyalkylenes, like polybutadiene-ethylenes, polybutadiene-propylenes, polyethylene-ethylenes; polyvinyl alcohols; polyalkylene glycols, like polyethylene glycols and polypropylene glycols; polydimethoxysiloxanes and polyurethanes.

In particular, the at least two blocks or components of the block copolymer are each of the (styrene/α-olefin) type, wherein the α-olefins of the two blocks can exhibit a different number of carbon atoms. The block copolymer is particularly chosen from the group of poly(styrene-ethylene/butene-styrene) and/or poly(styrene-ethylene/propylene-styrene). In particular the block copolymer can be a styrene/butadiene-block copolymer, styrene/butene-block copolymer, styrene/propylene-block copolymer, styrene/butene-propylene-block copolymer or styrene/rubber-block copolymer. According to the invention, useable styrene/rubber block copolymers are, for example, commercially available under the designation Kraton®, e.g., Kraton® G-1650 and Kraton® G-1651 from Kraton Polymers. The blocks of the abovementioned block copolymers can be arranged, for example, as triblock copolymers, star shaped or radially branched copolymers, multi-blocks of random polymers or grafted copolymers.

In the context of the inventive process, the gellable or hardenable oil phase is brought into contact with the stabilizer, particularly gel formers, in process step (b) preferably with stirring and/or at temperatures of 50° C. to 100° C., advantageously from 60° C. to 80° C., preferably at about 70° C., such that a liquid matrix medium is obtained, based on the oil phase and the stabilizer, particularly gel formers, resulting from process step (a). Finally, the liquid matrix medium obtained in process step (b) is optionally cooled, preferably to temperatures above the gel-formation temperature, particularly to temperatures of 25° C. to 50° C., advantageously from 35° C. to 45° C., preferably at about 40° C.

The cooling of the liquid matrix medium in process step (c) to temperatures above the gel-formation temperature is carried out with the aim of firstly preventing a gel formation before the incorporation of the percarboxylic acid being stabilized and secondly to at least largely eliminate a possible temperature dependent decomposition, in particular resulting from chemical decomposition, oxidation or reduction reactions and/or hydrolysis reactions or from possible temperature dependent dissolution of the percarboxylic acid being stabilized.

The organic percarboxylic acid being stabilized, which is incorporated in the form of solid particles into the preferably liquid matrix medium in process step (d), has a particle size or a particle diameter $\leq 3.000$ μm, particularly $\leq 2.500$ μm, advantageously $\leq 2.250$ μm, preferably $\leq 2.000$ μm, particularly preferably $\leq 1.500$ μm. In this context, the particle size of the organic percarboxylic acid should be 10 to 3.000 μm, particularly 50 to 2.500 μm, preferably 100 to 1.500 μm. According to the invention, the particle size of the solid percarboxylic acid particles and consequently the size of the gel capsules, can be adjusted in process step (e) by milling, e.g., stirring, vibration, ultrasound and/or shearing, such that a targeted match of particle or gel capsule size corresponding to their later use is possible.

The dispersion agent used in process step (e) can be a substance that is capable of dispersing the matrix medium from process step (d) with the incorporated, in particular dispersed solid particles of the organic percarboxylic acid being stabilized. Preferably, the dispersion agent incorporated in process step (e) is a polar substance, particularly water. However it is also possible to use glycerin as the dispersion agent, optionally mixed with water.

In this way in process step (e) the dispersion agent can be incorporated into the matrix medium and the matrix medium can also be incorporated into the dispersion agent.

In process step (e) the temperature is preferably below the gel formation temperature. In particular it is chosen in such a way that the matrix medium with the incorporated, in particular dispersed solid particles of the organic percarboxylic acid being stabilized, is still free-flowing. In particular, one should ensure that the temperature is chosen such that a temperature dependent decomposition or explosion of the organic percarboxylic acid being stabilized is avoided.

In the process step (e) of the inventive process, at least one dispersing agent (dispersant), particularly a surfactant dispersing agent, preferably a cationic and/or anionic surfactant can be added to the dispersion agent, particularly water. The dispersing agent should not contain, at least essentially, any halide ions, particularly any chloride ions. In particular, the quantity of halide ions in the dispersion of the solid percarboxylic acid in the preferably liquid matrix medium obtained in process step (e) should be maximum 500 ppm, particularly maximum 100 ppm, preferably maximum 30 ppm, as the organic percarboxylic acid being stabilized is decomposed faster in the presence of halide ions, particularly chloride—as is described in more detail below. In the inventive process, the cationic surfactant can be selected, for example, from the group of quaternary ammonium compounds, such as dimethyldistearylammonium salts; esterquats, particularly quaternized fatty acid trialkanolamine ester salts; salts of long chain primary amines; quaternary ammonium compounds, like hexadecyltrimethyl ammonium salts; cetrimonium salts and lauryldimethylbenzyl ammonium salts The anionic surfactant can be selected from the group of soaps; alkylbenzene sulfonates; alkane sulfonates; olefin sulfonates; alkyl ether sulfonates; glycerin ether sulfonates; α-methyl ester sulfonates; sulfofatty acids; alkyl sulfates; fatty alcohol ether sulfates; glycerin ether sulfates; fatty acid ether sulfates; hydroxy mixed ether sulfates; monoglyceride (ether) sulfates; fatty acid amide (ether) sulfates; mono- and dialkyl sulfosuccinates; mono- and dialkyl sulfosuccinamates; sulfotriglycerides; amide soaps; ether carboxylic acids and their salts; fatty acid isothionates; fatty acid arcosinates; fatty acid taurides; N-acylamino acids, such as acyl lactylates, acyl tartrates, acyl glutamates and acyl aspartates; alkyl oligoglucoside sulfates; protein fatty acid condensates, particularly vegetal products based on wheat; alkyl (ether) phosphates, wherein only halogen-free compounds should be used.

According to the invention, in process step (e), the capsule shell can be coated on the percarboxylic acid being stabilized, particularly imidopercarboxylic acid, in a device known to the expert, such as, for example a mixer, boiler etc.

The drying of the loaded gel capsules, optionally carried out in process step (g), can be accomplished using conventional methods, particularly by freeze-drying (lyophilization), evaporation of the dispersion agent, preferably at a temperature of 40° C. to 60° C., ultra filtration, dialysis or spray drying under gentle conditions.

In the context of the present invention, the capsule can be shaped and/or sized during or after the manufacturing process by, for example, shearing, droplet forming, prilling, pelletizing, briquetting, extrusion, cutting, rounding, granulation and the like, preferably in an appropriate device.

The gel capsules, loaded with at least one organic percarboxylic acid, particularly imidopercarboxylic acid, obtained according to the inventive process, can have an average size (diameter) of 0.01 mm to 5 mm, particularly 0.05 mm to 2 mm, preferably 0.1 to 1 mm.

Should the end-use require it or if desired, the gel capsules can be optionally separated according to their size, e.g., by classification, particularly sieving.

In the inventive process, the oil phase content is more than 80 wt. %, particularly more than 90 wt. %, preferably more than 95 wt. %, based on the oil phase/stabilizer-gel matrix. The stabilizer content, particularly gel former, is 0.1 wt. % to 20 wt. %, advantageously 0.3 wt. % to 5 wt. %, based on the oil phase/stabilizer-gel matrix. The organic percarboxylic acid content, particularly imidopercarboxylic acid, preferably PAP, is 30 wt. %, advantageously 40 wt. % and preferably 50 wt. %, based on the gel capsule. The oil phase/stabilizer-gel matrix therefore accounts for 1 to 70 wt. %, preferably 5 to 50 wt. %, based on the gel capsule. According to the end-use, a matching of the percarboxylic acid content should be undertaken, for example with a view to increasing the handling safety of the inventive gel capsules. On product safety grounds, too high a percarboxylic acid content may sometimes not be desired or practicable.

For these cases, the percarboxylic acid content should, for example, not exceed 50 wt. %, based on the gel capsule.

The gel capsules manufactured according to the inventive process possess a "controlled release effect". A "controlled release effect" is understood to mean a slightly delayed, preferably between 1 and 15 minutes, dissolution of the gel capsule during usage, for example in a wash liquor, or a time delay in releasing the percarboxylic acid from the inventive gel capsule.

In the scope of the inventive process, an additional shell can be coated onto the inventive gel capsules in a subsequent additional step, thereby producing a further stabilization effect with respect to the organic percarboxylic acid being stabilized. For example, a plasticizer and/or a chelatant that can complex heavy metal ions can be incorporated in the additional shell such that a heavy metal catalyzed decomposition of the percarboxylic acid can be largely prevented. The second shell can additionally serve to further modify the dissolution rate and to adjust this in a desired manner; in this way, an additional "controlled release effect" with respect to the percarboxylic acid contained in the inventive gel capsules can be achieved. The coating of the additional shell can be carried out by one of the methods known to the expert, e.g., the fluidized bed process or by adsorption of the additional shell material ("coating material") from a solution onto the gel capsule, spraying a solution or a melt of the coating material on the particle and subsequent evaporation of the solvent, preferably water, or by coating in a mixer, boiler etc. In this way, according to the invention, materials known to the expert can be added as additional coating substances, such as, for example inorganic compounds, e.g., salts and inorganic oxides, particularly sulfates or phosphates or even high-molecular weight compounds, such as organic polymers, e.g., cellulose ethers, polyvinyl alcohol (PVA), polyvinyl pyrrolidone (PVP) etc.

In the context of the present invention, the capsule shell and/or the additional shell of the inventive gel capsules can comprise at least one anti-dusting agent so as to reduce the stickiness of the material, its processability thereby being improved. The anti-dusting agent should not react with alkalis. According to the invention, exemplary preferred anti-dusting agents are sulfate salts and silica, e.g., Sipernat® from Degussa.

Furthermore, in the inventive process, the organic percarboxylic acid, for example, can be coated, preferably prior to the coating of the capsule shell, with a substance that in particular, can undergo endothermic reactions with itself, for example cleavage of water of crystallization or decomposition reactions at a temperature below 80° C., particularly below 70° C. According to the invention, this substance can also be blended with the percarboxylic acid, particularly compounded with it. Boric acid is an example of such a substance. In the context of the present invention, this substance can be added directly to the percarboxylic acid, preferably before coating the capsule shell, the same process steps being used as those for forming the additional shell, for example. The added substance leads to an increased handling safety of the inventive gel capsules, as it can quench or compensate for an eventual heat effect. "Heat effect" is understood to mean a local temperature increase in the gel capsules, which can develop due to a localized or initiating exothermic decomposition of the percarboxylic acid, as well as a temperature increase in a container or in the dispersion itself—for example during storage. The added substance, for example boric acid, can also be incorporated in the gel matrix or the gel capsule shell. However, according to the invention, a deposit onto the percarboxylic acid or a mixing or compounding with the percarboxylic acid is preferred, as this leads to an increased efficiency with regard to the handling safety.

The gel capsule dispersion or the gel capsules, resulting from process steps (e) and (f) respectively according to the inventive process, can be formulated, for example, together with further constituents to a washing or cleaning agent, particularly a liquid washing and cleaning agent. For this the washing or cleaning agent, at least essentially, should not comprise any halide ions, particularly chloride ions, or the amount of halide ions, particularly chloride ions, should be maximum 500 ppm, preferably maximum 100 ppm, particularly preferably maximum 30 ppm. The pH should be maximum 7, particularly between 3.5 and 7, preferably between 4.0 and 6.5, particularly preferably 4.5 and 6. Quite particularly preferably, the pH of the washing or cleaning agent should be about 5. In addition, the washing or cleaning agent can comprise at least one chelating agent; this can be selected for example from the group of quinoline and/or its salts, alkali metal polyphosphonates, picolinic acid and dipicolinic acid, mono- or polyphosphonic acids, particularly 1-hydroxyethylidene-1,1-diphosphonic acid (HEDP), ethylene diamine tetraacetic acid (EDTA), diethylene triamine penta(methylenephosphonic acid) (DTPMP), azacycloheptane diphosphonate (AHP), nitrilotriacetic acid (NTA), citrate and/or short chain dicarboxylic acids; in the context of the inventive process, these chelating agents are added particularly to complex heavy metal ions. In addition, the washing or cleaning agent can optionally comprise at least one water-miscible solvent which is a poor solvent for the organic percarboxylic acids, particularly the imidopercarboxylic acids (e.g., in amounts of preferably more than 20 wt. %, particularly preferably more than 30 wt. %, based on the washing or cleaning agent) or even the water-miscible solvent is the dispersion agent or the dispersion. The solvent can be glycerin for example, which is a poor solvent for PAP. However, according to the invention, the preferred solvent is water. In addition, at least one catalase, at least one peroxidase and/or at least one antioxidant can be optionally added to the washing or cleaning agent. For further details of the washing or cleaning agent, reference can be made to the following embodiments.

The inventive process is likewise a process for stabilizing percarboxylic acids, particularly imidopercarboxylic acids, preferably PAP, and a process for increasing the storability of percarboxylic acids, particularly imidopercarboxylic acids, preferably PAP.

According to a typical embodiment, the inventive process can be carried out as follows: Paraffin is used to protect the percarboxylic acid, particularly imidopercarboxylic acid (e.g., PAP), however, no paraffin having a high melting point is used, as firstly, this does not enable a fast enough release of the PAP in the washing process and secondly it can form tenacious residues on the washing and is deposited in the form of solid or "greasy" particles on the textiles. Thus, according to the invention, a paraffin oil is advantageously added, which is liquid at room temperature. This can be easily dissolved from the textiles present in the washing process. In order to have an adequate mechanical stability, the paraffin oil should be gelled with a lowest possible concentration of stabilizer or gel former; block copolymers for example, are suitable for this, those consisting of a stiff block, a flexible block and another stiff block being preferred. Exemplary suitable polymers are those of the type poly(styrene-ethylene/butene-styrene) or poly(styrene-ethylene/propylene-styrene) which are available under the designations Kraton®, e.g., Kraton® G-1650. The oil phase/stabilizer-gel matrix or the gel capsules, in which the bleaching agents are incorporated, can be manufactured in particular in the following manner: Firstly, a solution of the gel-forming polymer in paraffin oil is prepared at a temperature above the gel formation temperature (e.g., 50° C. to 100° C.). This solution is cooled down to about 40° C. and subsequently the bleaching agent (percarboxylic acid) is dispersed in it. The resulting dispersion ("slurry") should still be free flowing, yet as cold as possible to avoid any decomposition of the percarboxylic acid. Finally this dispersion is dispersed in water into which has been optionally added some surfactant as dispersing agent. The mechanics of the dispersion enable the particle size to be adjusted. Encapsulated percarboxylic acid or an oil phase/stabilizer-gel matrix furnished with percarboxylic acid (e.g., PAP) can be separated from any excess paraffin by means of an optional, subsequent centrifugation. The particles can then, e.g., be transferred into a washing agent formulation, preferably into a liquid washing agent formulation. In the simplest case, the dispersion, containing gel capsules, can be directly processed further, i.e. without separating the gel capsules.

A further subject—according to a second aspect of the invention—concerns the gel capsules loaded with at least one organic percarboxylic acid, particularly imidopercarboxylic acid (e.g., PAP), and manufacturable according to the inventive process. They comprise at least one organic percarboxylic acid, particularly imidopercarboxylic acid, preferably PAP, incorporated into a gel matrix that is used as the encapsulate or as a coating. The encapsulant or coating, which surrounds the percarboxylic acid comprises an oil phase that is inert towards the organic percarboxylic acid, and hardened or gelled by the addition of at least one stabilizer, particularly gel formers.

In relation to the nature of the oil phase and the block copolymers, which form the gel matrix for the percarboxylic acid, reference can be made to the above statements on the inventive process, which are correspondingly valid.

The organic percarboxylic acid to be stabilized is particularly chosen from organic mono- and dipercarboxylic acids, particularly dodecaneperdioic acid and preferably imidopercarboxylic acids, particularly preferably 6-phthalimidopercapric acid (6-phthalimidoperhexanoic acid, PAP). The percarboxylic acid should have a melting point at atmospheric pressure above 25° C., particularly above 35° C., advantageously above 45° C., preferably above 50° C., particularly preferably above 100° C.

The formation of the gel matrix in the inventive gel capsules can result from physical and/or chemical interactions, e.g., due to physical network formation between the oil phase on the one hand and the stabilizer, particularly gel formers, on the other hand.

According to the invention, the encapsulation or the coating surrounding the percarboxylic acid to be stabilized is such that the percarboxylic acid to be stabilized is at least essentially totally enclosed, such that the percarboxylic acid is not in direct contact with the surrounding milieu, in particular the dispersion agent, i.e. the percarboxylic acid to be stabilized, is in the inventive gel capsule preferably as the core material, which is surrounded by the gel matrix.

When needed or desired for end-use applications, further additives or auxiliaries (e.g., substances which are used to increase the handling safety, such as boric acid, stabilizers, modifiers, inorganic salts, colorants etc.) can be added to the core material (percarboxylic acid) and/or the gel matrix or the gel capsule shell.).

The gel capsules according to the present invention comprise an oil phase content of more than 80 wt. %, particularly more than 90 wt. %, preferably more than 95 wt. %, based on the oil phase/stabilizer-gel matrix. The stabilizer content, particularly gel former, is 0.1 wt. % to 20 wt. %, advantageously 0.3 wt. % to 5 wt. %, based on the oil phase/stabilizer-gel matrix. The organic percarboxylic acid content, particularly imidopercarboxylic acid, preferably PAP, is 30 wt. %, advantageously 40 wt. % and preferably 50 wt. %, based on the gel capsule. Thus the oil phase/stabilizer-gel matrix represents 1 to 70 wt. %, preferably 5 to 50 wt. %, based on the gel capsule.

For further details concerning the inventive gel capsules, reference can be made to the above statements on the inventive process, which are correspondingly valid here.

The end-use possibilities of the inventive gel capsules are very numerous and widespread. Thus, the inventive gel capsules—according to a further aspect of the present invention—can be added in washing and cleaning agents, particularly in liquid washing and cleaning agents, tooth-care products, hair colorants and decolorizing or bleaching agent compositions for technical uses.

The inventive gel capsules can also be used as delivery systems for the controlled release of percarboxylic acids, wherein the controlled release of the percarboxylic acids can result from the choice and/or quantity of the composition of the gel capsules. According to the invention, "composition" is hereby understood to mean particularly the type and/or quantity of the block copolymer or the type and/or quantity of the oil phase or the type and/or quantity of the percarboxylic acid to be encapsulated. In this way the release of the percarboxylic acid can be controlled, especially by controlling the glass transition temperature of the polymer blocks of the block copolymer and thereby the gel formation temperature $T_{gel}$ of the gel capsules. A further possibility for modification is illustrated by depositing an additional shell ("coating") onto the inventive gel capsules.

In particular, the inventive gel capsules can be used as "delivery systems", in which the percarboxylic acids are given off over a long period of time by means of an extended and/or decreased release ("sustained release effect").

A further subject of the present invention—according to a further aspect of the present invention—are washing and cleaning agents, particularly liquid washing and cleaning agents, tooth-care products, hair colorants and decolorizing or bleaching agent compositions for technical uses, which comprise the inventive gel capsules loaded with at least one percarboxylic acid, particularly imidopercarboxylic acid.

Tooth-care products can be particularly those that are used to brighten or whiten teeth. Concerning hair dyes, examples are those products based on bleaching agents that are added particularly for lightening or coloring hair. For the inventive decolorizing or bleaching agent compositions for technical uses, examples comprise such agents that are used both in the household as well as in the industrial arena for diverse applications, which require a certain bleach performance, such as, e.g., removal or decolorization of paints and/or lacquers or other contaminants.

The inventive washing and cleaning agents, which comprise the inventive gel capsules, can be used in the household as well as in the industrial domain. The washing and cleaning agents are particularly liquid washing and cleaning agents that comprise the inventive gel capsules.

The inventive washing and cleaning agents can be used for cleaning hard surfaces and/or softer, especially textile surfaces. The inventive washing and cleaning agents can be used especially as dishwasher agents, general purpose cleaners, bath cleaners, floor cleaners, automobile cleaners, glass cleaners, furniture care agents or cleaners, facade cleaners, detergents or the like, particularly preferably as detergents. In addition, the inventive washing and cleaning agents are advantageously suited for cleaning fibers, textiles, carpets and the like.

The inventive washing and cleaning agents comprise, in addition to the inventive gel capsules, usual constituents (e.g., surfactants, fragrences, colorants, enzymes, enzyme stabilizers, builders, pH-adjusters, other bleaching agents, bleach activators, silver protection agents, soil repellents, optical brighteners, graying inhibitors, disintegration auxiliaries, defoamers or foam inhibitors, chelating agents for heavy metals, soil repellents, color transfer inhibitors, solvents, optical brighteners and/or optional further usual ingredients etc.), wherein in the context of the present invention, care should be taken concerning the compatibility of the individual ingredients or components, both among themselves as well as in regard to the inventive gel capsules or the percarboxylic acids contained therein, which can be realized by judicious choices of ingredients or components and/or their relative proportions. In this manner, an unwanted interaction of these ingredients or components with the inventive gel capsules or the percarboxylic acids incorporated therein can be avoided. As is disclosed in greater detail below, the judicious choice of specific ingredients or components and/or their relative proportions can afford a stabilizing effect with respect to the inventive gel capsules or the percarboxylic acids incorporated therein.

An inventive washing or cleaning agent, especially a liquid washing or cleaning agent, comprises, for example, the following ingredients:
(a) a gel capsule, according to the present invention, loaded with at least one organic percarboxylic acid, particularly imidopercarboxylic acid, preferably in amounts of 0.1 wt. % to 30 wt. %; and/or
(b) surfactants, particularly cationic and/or anionic surfactants, preferably in amounts of 5 to 30 wt. %, and/or non-ionic surfactants, preferably in amounts of 0 to 30 wt. %, and/or
(c) optional electrolytes, particularly inorganic and/or organic salts, preferably sodium sulfate, preferably in amounts of 0 to 30 wt. %; and/or
(d) optional chelating agents, particularly selected from the group of quinoline and/or its salts, alkali metal polyphosphonates, picolinic acid and dipicolinic acid, mono- or polyphosphonic acids, particularly 1-hydroxyethylidene-1,1-diphosphonic acid (HEDP), ethylene diamine tetraacetic acid (EDTA), diethylene triamine penta(methylenephosphonic acid) (DTPMP), azacycloheptane diphosphonate (AHP), nitrilotriacetic acid (NTA), citrate and/or short chain dicarboxylic acids, preferably in amounts of 0 to 5 wt. %; and/or
(e) optional enzymes, such as proteases, amylases, cellulases and/or lipases, optionally together with enzyme stabilizers, preferably in amounts of 0 to 10 wt. %: and/or
(f) optional builders, particularly fatty acids, preferably saturated and/or branched fatty acids, advantageously with a melting point below 30° C., and/or citric acid and/or citrate, preferably in amounts of 0 to 15 wt. %; and/or
(g) optional fragrances, preferably in amounts of 0 wt. % to 5 wt. %; and/or
(h) optional auxiliaries, such as foam inhibitors, pH-regulators, rheology modifiers (thickeners), solvents, colorants; and/or
(I) optional additional ingredients, such as brighteners etc.; and/or
(j) water;

wherein all the specified weights are based on the washing or cleaning agent.

In the washing and cleaning agents, particularly in liquid washing and cleaning agents, the surfactants in the washing and cleaning agent formulations may be inactivated, particularly by salting out, i.e. the induction of a phase separation into a surfactant-poor, continuous phase and a preferably lamellar, generally high-viscosity, crystalline or liquid-crystalline surfactant-rich phase, preferably by incorporating a sulfate compound, particularly preferably sodium sulfate, into the washing or cleaning agent formulation. Thus, in particular, a dissolution or solubilization of the oil phase of the gel capsule or the organic percarboxylic acid, particularly imidopercarboxylic acid in the washing or cleaning agent formulation is at least extensively hindered or prevented. According to the invention, the term "continuous phase" is understood to mean the dispersion agent with the components or ingredients (e.g., salts, surfactants etc.) dissolved therein. According to the invention, the preferred dispersion agent is water.

In this context, Applicants have shown that organic percarboxylic acids, particularly PAP, are rapidly decomposed in the presence of active surfactants (i.e. surfactants, present in free and/or micellar form in the washing or cleaning agent formulation), as the percarboxylic acids, due to the surfactants, are better dissolved and are extremely unstable in this dissolved state. In this context, particularly non-ionic surfactants or niosurfactants, e.g., based on alkyl polygcolethers, lead to an accelerated decomposition of the percarboxylic acids. Without wishing to be bound by any theory, the instability of the percarboxylic acids in the presence of surfactants can be attributed to the generally strong nucleophilicity of the percarboxylic acids, which are reduced to the corresponding carboxylic acids with the evolution of oxygen. The addition of sulfate at least partially inactivates the surfactants, as happens in particular on salting out, the surfactants being transported out of the particularly micellar, active form into a preferably lamellar, crystalline or liquid-crystalline form (crystal formation or liquid crystal formation) that is dispersed in a preferably almost surfactant-free continuous phase. The dispersed liquid crystals, themselves, which can be separated by centrifugation, for example, should have a high viscosity. The free surfactant content in the inventive washing and cleaning agent formulations or in the continuous phase of the washing and cleaning agent formulations should be preferably 1% at most.

The sulfate concentration in the inventive washing or cleaning agents should be chosen such that on using the washing or cleaning agent in the washing liquor, the surfactants are once more present in active form, which can be achieved, for example, through the dilution effect when the washing or cleaning agent is incorporated into the washing liquor. In particular, the concentration should be chosen such that—as previously mentioned—less than 1% of dissolved surfactant is present in the continuous phase of the undiluted washing or cleaning agent and no sulfate crystallizes out on lowering the temperature, particularly down to 0° C.

As non-ionic surfactants in particular can be problematic in regard to the stability of percarboxylic acid, the inventive washing and cleaning agents have an appropriately matched or optimized niosurfactant/total surfactant ratio. Here, the alkyl polyglycol ether content should be as low as possible.

In the context of the present invention, the inventive washing and cleaning agents, particularly liquid washing and cleaning agents should not comprise, at least substantially, any halide ions, particularly chloride ions. Advantageously, the amount of halide ions, particularly chloride ions, is maximum 500 ppm, preferably maximum 100 ppm, particularly preferably maximum 30 ppm. Applicants have surprisingly discovered that a high halide, especially chloride concentration, as is commonly found in conventional washing and cleaning agents, due to the contaminants in some raw materials and ingredients, leads to an increased decomposition of percarboxylic acids. Therefore, a reduction in the halide, especially chloride ion concentration, can lead to a reduced decomposition of the percarboxylic acid. According to the invention, a low chloride ion concentration can be achieved particularly by the addition of compounds of methyl sulfate, phosphate, tosylate or cumene sulfonate. Moreover, raw materials and ingredients should be selected that have a particularly low chloride content (e.g., the use of essentially halide-free components, e.g., halide-free surfactants, halide-free phosphonates etc.)).

In addition, the inventive washing and cleaning agents should have a pH of maximum 7, particularly a pH of 3.5 to 7, preferably from 4.0 to 6.5, particularly preferably from 4.5 to 6, quite particularly preferably of about 5. Surprisingly, bleaching agents based on percarboxylic acids, such as PAP, can be relatively efficiently stabilized in an acidic environment, particularly at a pH$\leq$3.5, whereas at neutral or alkaline pH a relatively rapid decomposition takes place. The reduction in pH in the inventive washing and cleaning agents can be achieved by adding acids or acidic salts. Bisulfates and/or bicarbonates or organic polycarboxylic acids that can be also used simultaneously as, e.g., builders, are preferred. Moreover, phosphonates used as chelating agents, can be added as phosphonic acids and subsequently adjusted to the desired pH by the addition of alkalis.

The inventive washing or cleaning agents can comprise at least one fatty acid. According to the invention, saturated and/or branched fatty acids, particularly with a melting point below 30° C., are preferred. In the context of the present invention, Isocarb-16® from the Sasol company, for example, can be used in the inventive washing or cleaning agents.

The inventive washing or cleaning agents possess an optimized content of citric acid or citrate. As Applicants have discovered, citric acid or citrate can lead to a decomposition of percarboxylic acids, particularly PAP. Nevertheless, if need be, it may be necessary to add citric acid or citrate in the washing or cleaning agent or in the dispersion agent for the inventive gel capsules (e.g., as the builder and/or as the chelating agent). However, the amounts used should not be too high and should be adapted to the percarboxylic acid, particularly PAP.

In addition, the inventive washing or cleaning agent can comprise at least one chelating agent, which can be particularly selected from the group of quinoline and/or its salts, alkali metal phosphonates, picolinic acid or dipicolinic acid, mono- or polyphosphonic acids, particularly 1-hydroxyethylidene-1,2-diphosphonic acid (HEDP), ethylene diamine tetraacetic acid (EDTA), diethylene triamine penta(methylenephosphonic acid) (DTPMP), azacycloheptane diphosphonate (AHP), nitrilotriacetic acid (NTA), citrate and/or short chain dicarboxylic acids. Further examples for inventively useable chelating agents for heavy metals are, e.g., aminopolycarboxylic acids, aminohydroxypolycarboxylic acids, polyphosphonic acids and aminopolyphosphonic acids. According to the invention, these chelating agents are added to complex the heavy metal ions that act particularly as catalysts for oxidation processes and can lead to a decomposition of percarboxylic acids, such as PAP and which can be incorporated for example from water pipes or metallic components of the production units or from raw materials or ingredients into the inventive washing or cleaning agents.

Moreover, the inventive washing and cleaning agents can optionally comprise at least one water-miscible solvent, in which the organic polycarboxylic acids are poorly soluble, such as preferably glycerin.

Furthermore, the inventive washing and cleaning agents can optionally comprise at least one catalase, if needed, so as to efficiently remove hydrogen peroxide, resulting from the reaction of percarboxylic acid with water, from the continuous phase of the product, particularly the washing and cleaning agent formulation, such that particularly the optionally present enzymes are efficiently protected against oxidation processes that could possibly lead to a loss of activity of the enzymes. With this objective, at least one peroxidase and/or at least one antioxidant, optionally in addition to the at least one catalase, can similarly be added to the inventive washing or cleaning agents. According to the invention, preferred antioxidants are, e.g., ascorbic acid, tocopherol, gallic acid or their derivatives.

In addition, the inventive washing or cleaning agent formulation should be designed in such a way that they, in particular, essentially do not dissolve or attack the inventive gel capsules. In general, the additional components, which are used in the inventive washing or cleaning agent, should be chosen with the proviso that they are at least largely compatible with respect to the inventive gel capsules, i.e. particularly in the washing or cleaning agent itself, particularly in the period before its utilization (storage time), there should be no unwanted chemical reactions, such as in particular degradation, oxidation or reduction and/or hydrolytic reactions between these components and the gel capsules, which would lead to a premature decomposition and a loss in activity of the percarboxylic acid.

In order to obtain an adequate bleaching power in the washing liquor, the percarboxylic acid should be released sufficiently quickly from the inventive gel capsules. The percarboxylic acid is released during the utilization of the washing or cleaning agent, particularly by physical or physicochemical processes, for example solubilization, emulsification or dissolution of the oil phase/stabilizer-gel matrix in the washing liquor or by osmotic phenomena or diffusion processes. At the same time it should be ensured that in the washing or cleaning agent itself, no release of the percarboxylic acids occur, in particular a separation or dissolution or solubilization of the oil phase/stabilizer-gel matrix does not take place or that the percarboxylic acid can be dissolved or diffuse out of the gel capsule by osmosis.

During utilization of the inventive gel capsules, the percarboxylic acid is released by dissolution of the network or gel made of oil phase and stabilizer, particularly gel former. For the case of, e.g., a washing or cleaning agent concentrate, which comprises the inventive gel capsules as well as surfactants in inactivated form (e.g., by salting out for example, with sodium sulfate or in the form of liquid crystals), then as the concentrate is diluted in the course of its use in the washing liquor, the surfactants are transformed from their inactivated or salted out form into their active form, such that the surfactants, activated in this way, can solubilize or dissolve or attack the gel capsule shell or the gel matrix. On dilution in the washing liquor, a jump in pH occurs, resulting in a marked increase in solubility of the percarboxylic acid. Moreover, diffusion processes appear (e.g., diffusion of water molecules through the gel capsule shell) that in the same way lead to dissolution of the gel capsule shell during usage. Osmotic phenomena also play a role. Finally, mechanical phenomena are also of importance, e.g., mechanical destruction of the gel capsule by the washing in the washing liquor or by contact with the washing drum.

As previously mentioned, a controlled release of the percarboxylic acid results from the particular structure or the particular design of the inventive gel capsules.

Compared with the prior art, the present invention shows a series of advantages:

The formation of the oil phase/stabilizer-gel matrix occurs in the inventive process as a result of physico-chemical or physical interactions, such that no polymerization steps, especially radical polymerization steps are required for the formation of the capsule structure, as is the case for several processes of the prior art. Such types of polymerization often lead to the decomposition of the active materials and/or active agents, especially the sensitive percarboxylic acid. The present invention thus provides an encapsulation process in line with the chemically sensitive percarboxylic acid.

In addition, the inventive process has the advantage that it provides gel capsules loaded with percarboxylic acids, especially imidopercarboxylic acids and whose size and active substance contents can be widely varied or tailor-made, with the result that they can be matched to each application, especially in the domain of washing and cleaning agents. In this context, it is particularly advantageous that the proportion of oil phase/stabilizer-gel matrix to the content of organic percarboxylic acid can be matched, such that the gel capsules can be adapted to the sensitivity of the percarboxylic acid to be encapsulated. Moreover, the controlled adjustable sizes of the capsules make possible an effective dosage of the active material as a function of its application. According to the invention, a small amount of starting material(s) can be used for the gel matrix, enabling gel capsules with a high content of percarboxylic acid to be realized.

Contrary to encapsulation systems that are based, for example on waxes, the inventive gel capsules do not contain any troublesome capsule shells that lead to unwanted residues on the washing in washing processes.

The inventive gel capsules possess a decisive advantage in that they have a markedly increased storage stability as compared with systems of the prior art and thus dispose of a high bleaching activity even after longer periods.

In particular, the inventive gel capsules are suitable for mixing or application in surfactant-containing systems, for example surfactant-containing dispersions for liquid washing and cleaning agents. This is a particular advantage as the unencapsulated or unprotected percarboxylic acids, particularly PAP, are unstable in the presence of surfactants and are rapidly decomposed, such that their use in surfactant-containing liquid, particularly aqueous media was not possible up to now or was at the most of very limited possibility. The stabilizing effect of the gel capsules, which is additionally linked with a desirable controlled release of the encapsulated percarboxylic acid, can be synergistically increased by adjusting the medium in which the gel capsules are present in such a way as to obtain an additional stabilization of the percarboxylic acid, particularly by inactivating the surfactants, optimizing or reducing the pH, reducing the halide content, using a solvent that is a poor solvent for percarboxylic acids and the like.

The inventive gel capsules can be stably incorporated particularly in liquid washing and cleaning agents. An additional prevention or reduction of sedimentation processes can for example be achieved by means of suitable thickening systems known to the expert. In the liquid washing and cleaning agents, the gel capsule possess a high storage stability and can efficiently release the percarboxylic acids even after longer periods of time.

Due to their adjusted and synergistically acting modifications on each other listed above, i.e. formulation matching, in particular lower halide ion content, optimization of the pH, addition of chelating agents, specific solvents or enzymes, such as catalases or peroxidases, addition of antioxidants, inactivation of surfactants, the inventive washing and cleaning agent formulations possess substantial advantages compared with the prior art, as in combination with the inventive gel capsules the decomposition of the sensitive bleaching agent based on percarboxylic acid is markedly reduced.

Further developments, modifications and variations as well as advantages of the present invention are directly recognizable and realizable for the expert on reading the description, without him thereby leaving the scope of the present invention.

The present invention is clarified by means of the following exemplary embodiments, which in no way limit the invention.

EXAMPLES

Example 1: Manufacture of the Inventive Encapsulated or Coated Bleaching Agent Particles Low viscosity paraffin oil was heated to 70° C. and 2% Kraton® G-1650 was added. It was stirred until a homogeneous solution was obtained. The mixture was cooled to 40° C. and 60% of homogenized Eureco® W, based on paraffin oil/Kraton, was added with stirring. This mixture was then stirred into five times the amount of water and cooled down. The resulting dispersion was centrifuged. The encapsulated or coated PAP particles sink to the bottom while the excess paraffin floats on the surface. The PAP-containing particles were removed, dried and sieved to <1 mm. The PAP content was 50%. They were processed further, as described in Example 2. The production of the encapsulated or coated bleaching agent particles can be carried out in a mixer. In addition, the capsule shell can comprise an anti-dusting agent, such as a sulfate salt.

Example 2

The encapsulated or coated bleaching agent particles manufactured in Example 1 were incorporated into the following liquid composition (the percentages are active material values):

| | |
|---|---|
| LAS (Marsnil ® A 55 (Cognis)) | 22.5% |
| Dehydol ® LT 7 (Cognis) | 4% |
| Na$_2$SO$_4$ | 12.5% |
| Xanthan Gum | 0.5% |
| Sequion ® 10 H 60 (Polygon Chemie AG) | 1% |
| Water | ad 100% |

Using Sequion®, the pH was adjusted to 5.0 by back titration with sodium hydroxide.

Example 3

Composition of a further liquid formulation, in which the encapsulated or coated bleaching agent particles can be incorporated:

| | |
|---|---|
| LAS (Marsnil ® A 55 (Cognis)) | 18.5% |
| Dehydol ® LT 7 (Cognis) | 8% |
| Sodium sulfate | 11% |
| Xanthan gum | 0.4% |
| Sequion ® 10 H 60 (Polygon Chemie AG) | 1% |
| Silicone defoamer | 0.2% |
| Capsule system of Example 1 | 3% |
| Water | ad 100% |

Comparative Example

Untreated Eureco® W (3.5%) was incorporated into the liquid composition according to EXAMPLE 2. The pH was also 5.0. The residual active oxygen content (100% at start of storage) was determined after various storage times at 40° C. by means of iodometric titration.

One obtains:

| | Inventive | Comparative Example |
|---|---|---|
| 1 week | 100.0% | 87.5% |
| 2 weeks | 99.2% | 80.0% |

It can be seen that the stability of PAP with the inventive encapsulation or coating is markedly increased.

The invention claimed is:

1. A process for the manufacture of a gel capsule, loaded with at least one organic percarboxylic acid comprising the steps of: (a) providing an oil having a melting point below 35° C. at atmospheric pressure and that is inert towards the organic percarboxylic acid; (b) contacting the oil with at least one stabilizer at a temperature of from 25° C. to 50° C. to obtain a liquid matrix medium comprising the oil and the stabilizer, (c) optionally cooling the matrix medium resulting from step (b) to a temperature above the gel-formation temperature of the matrix medium; (d) incorporating at least one organic percarboxylic acid in the form of solid particles into the liquid matrix medium obtained in step (b) to form a dispersion of the solid percarboxylic acid in the liquid matrix medium; (e) contacting the matrix medium obtained in process step (d), with a dispersion agent at a temperature below the gel-formation temperature to form gel capsules, wherein the organic percarboxylic acid is incorporated in an oil /stabilizer-gel matrix.

2. The process of claim 1 further comprising the step of (f) removing, the dispersion agent and any excess oil phase from the gel capsule dispersion obtained from process step (d).

3. The process of claim 1 further comprising the step (g) of drying the gel capsules formed.

4. The process of claim 1, wherein the organic peroxycarboxylic acid is an organic mono- and diperoxycarboxylic acid.

5. The process of claim 4, wherein the organic diperoxycarboxylic acid is dodecanediperoxy acid.

6. The process of claim 1, wherein the organic peroxycarboxylic acid has a melting point at atmospheric pressure above 25° C.

7. The process of claim 1, wherein the organic peroxycarboxylic acid is an imidoperoxycarboxylic acid.

8. The process of claim 7, wherein the imidoperoxycarboxylic acid 6-phthalimidoperoxycaproic acid.

9. The process of claim 1, wherein the oil is selected from the group of paraffin oils, isoparaffin oils, silicone oils, glycerides, triglycerides, naphthalene-containing oils, hydrocarbon-containing solvents and their mixtures, vegetal oils, castor oil, maize oil, peanut oil, alkyl palmitates and alkyl alcohol benzoates.

10. The process of claim 1, wherein the stabilizer is a block copolymer having at least two blocks wherein at least one of the blocks is a hard block and at least one other block is a soft block wherein the glass transition temperatures of the hard and soft blocks differ by at least 50° C.

11. The process of claim 10, wherein the hard block is slightly oil-soluble and the soft block is oil-soluble.

12. The process of claim 10, wherein the hard block is selected from the group of polystyrenes, poly(meth)acrylates, polycarbonates, polyesters, polyanilines, poly-p-phenylenes, polysulfone ethers, polyacrylonitriles, polyamides, polyimides, polyethers, polyvinyl chlorides and their mixtures and/or the soft block is selected from the group consisting of polybutadienes, polybutadiene-ethylenes, polybutadiene-propylenes, polyethylene-ethylenes; polyvinyl alcohols; polyalkene glycols, polydimethoxysiloxanes and polyurethanes.

13. The process of claim 10, wherein the block copolymer is selected from the group consisting of poly(styrene-ethylene/butene-styrene), poly(styrene-ethylene/propylene-styrene) a styrene/butadiene block copolymer, styrene/butene block copolymer, styrene/propylene block copolymer, styrene/butene-propylene block copolymer and styrene/rubber block copolymer.

14. The process of claim 1, wherein the stabilizer is a metal soap, an alkyl hydroxybutyramide or a layered silicate.

15. The process of claim 1, wherein the oil phase is brought into contact with the stabilizer step (b) with stirring and at a temperature above from 50° C. to 100° C.

16. The process of claim 1, wherein the matrix medium is cooled in process step (c) to a temperature of from 25° C. to 50° C.

17. The process of claim 1, wherein the particle size of the peroxycarboxylic acid solid particles is $\leq 3000$ μm.

18. The process of claim 1, wherein the dispersing agent comprises a cationic surfactant selected from the group consisting of dimethyldistearylammonium salts; quaternized fatty acid trialkanolamine ester salts; salts of long chain primary amines; hexadecyltrimethyl ammonium salts; cetrimonium salts and lauryldimethylbenzyl ammonium salts; and/or an anionic surfactant selected from the group consisting of alkylbenzene sulfonates, alkane sulfonates, olefin sulfonates, alkyl ether sulfonates, glycerin ether sulfonates, α-methyl ester sulfonates, sulfofatty acids, alkyl sulfates, fatty alcohol ether sulfates, glycerin ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and their salts, fatty acid isothionates, fatty acid arcosinates, fatty acid taurides, acyl lactylates, acyl tartrates, acyl glutamates, acyl aspartate, alkyl oligoglucoside sulfates, vegetal products based on wheat, and alkyl (ether) phosphates and wherein the concentration halide ions is less than 500 ppm.

19. The process of claim 1, wherein in step (e) the gel capsule is formed into particles by shear forces.

20. The process of claim 3, wherein the separation is carried out by freeze-drying, evaporation of the dispersion agent, ultra filtration, dialysis or spray drying.

21. The process of claim 3, further comprising the step (h), wherein the capsule is shaped by shearing, droplet formation, prilling, pelletizing, briquetting, extrusion, cutting, rounding, or granulation.

22. The process of claim 8, wherein the gel capsule has spherical diameter of from 0.01 to 5 mm and an imidopercarboxylic acid content of $\geq 30$ wt. %.

23. The process of claim 1, wherein the organic peroxycarboxylic acid has a melting point at atmospheric pressure above 35° C.

* * * * *